(12) United States Patent      (10) Patent No.: US 8,268,838 B2
Eriksen et al.      (45) Date of Patent: Sep. 18, 2012

---

(54) SUBSTITUTED PURINYL-PYRAZOLE DERIVATIVES AND THEIR USE AS POTASSIUM CHANNEL MODULATORS

(75) Inventors: Birgitte L. Eriksen, Farum (DK); Charlotte Hougaard, Bagsværd (DK); Dan Peters, Malmö (SE); Palle Christophersen, Ballerup (DK)

(73) Assignee: Neurosearch A/S, Ballerup (DK)

( * ) Notice: Subject to any disclaimer, the term of this patent is extended or adjusted under 35 U.S.C. 154(b) by 0 days.

(21) Appl. No.: 13/120,833

(22) PCT Filed: Sep. 22, 2009

(86) PCT No.: PCT/EP2009/062253
§ 371 (c)(1), (2), (4) Date: Jun. 13, 2011

(87) PCT Pub. No.: WO2010/034707
PCT Pub. Date: Apr. 1, 2010

(65) Prior Publication Data
US 2011/0251217 A1    Oct. 13, 2011

Related U.S. Application Data

(60) Provisional application No. 61/100,975, filed on Sep. 29, 2008.

(30) Foreign Application Priority Data

Sep. 26, 2008 (DK) .................. 2008 01331

(51) Int. Cl.
    *C07D 473/16*      (2006.01)
    *A61K 31/52*      (2006.01)
    *C07D 473/40*      (2006.01)

(52) U.S. Cl. .................. 514/263.2; 544/277; 564/218
(58) Field of Classification Search ............. 544/277; 514/263.2
See application file for complete search history.

(56) References Cited

U.S. PATENT DOCUMENTS

| | | | |
|---|---|---|---|
| 6,743,798 B1 * | 6/2004 | Straub et al. ............ | 514/263.2 |
| 7,091,346 B1 | 8/2006 | Zimmermann et al. | |
| 2002/0068721 A1 | 6/2002 | Weigele et al. | |
| 2003/0139427 A1 | 7/2003 | Castelhano et al. | |
| 2004/0116376 A1 | 6/2004 | Elzein et al. | |
| 2005/0124637 A1 * | 6/2005 | Cheng et al. ............ | 514/263.2 |
| 2008/0242683 A1 | 10/2008 | Fairhurst et al. | |
| 2008/0275045 A1 | 11/2008 | Eriksen et al. | |
| 2009/0036475 A1 | 2/2009 | Eriksen et al. | |
| 2009/0306102 A1 | 12/2009 | Eriksen et al. | |
| 2009/0325989 A1 | 12/2009 | Eriksen et al. | |
| 2010/0056494 A1 * | 3/2010 | Winzeler et al. ......... | 514/263.2 |
| 2010/0105705 A1 * | 4/2010 | Eriksen et al. ............ | 514/263.22 |
| 2010/0120797 A1 * | 5/2010 | Eriksen et al. ............ | 514/263.1 |
| 2010/0130516 A1 * | 5/2010 | Eriksen et al. ............ | 514/263.2 |
| 2010/0152210 A1 | 6/2010 | Eriksen et al. | |
| 2010/0183564 A1 * | 7/2010 | Boitano et al. ............ | 514/263.2 |
| 2010/0197914 A1 * | 8/2010 | Fairhurst ................ | 544/277 |
| 2011/0237607 A1 * | 9/2011 | Eriksen et al. ............ | 514/263.2 |
| 2011/0251217 A1 * | 10/2011 | Eriksen et al. ............ | 514/263.2 |
| 2012/0004246 A1 * | 1/2012 | Eriksen et al. ............ | 514/263.2 |

FOREIGN PATENT DOCUMENTS

| | | |
|---|---|---|
| WO | WO 01/44259 A1 | 6/2001 |
| WO | WO 01/44260 A2 | 6/2001 |
| WO | WO 03/075828 A2 | 9/2003 |
| WO | WO 2006/097441 A1 | 9/2006 |
| WO | WO 2006/100212 A1 | 9/2006 |
| WO | WO 2006/125211 A1 | 11/2006 |
| WO | WO 2007/017632 A2 | 6/2007 |
| WO | WO 2008/040753 A1 | 4/2008 |
| WO | WO 2008/116909 A1 | 10/2008 |
| WO | WO 2008/116910 A1 | 10/2008 |

(Continued)

OTHER PUBLICATIONS

International Search Report, dated Nov. 3, 2009, issued in corresponding International Application PCT/EP2009/062253.
Brown et al., "Heterocyclic Amplifiers of Phleomycin. VI. Some Phenylpurines, Phenylpteridines, Phenylquinazolines and Related Compounds", Australian Journal of Chemistry, 1985, vol. 38, pp. 467-474.

(Continued)

*Primary Examiner* — Mark Berch
(74) *Attorney, Agent, or Firm* — Birch Stewart Kolasch & Birch, LLP

(57) ABSTRACT

Provided are substituted purinyl-pyrazol derivatives of the following formula (I), or a pharmaceutically acceptable salt thereof, and their use as potassium channel modulating agents, as well as pharmaceutical compositions having such derivatives that are useful for the treatment or alleviation of diseases or disorders associated with the activity of potassium channels:

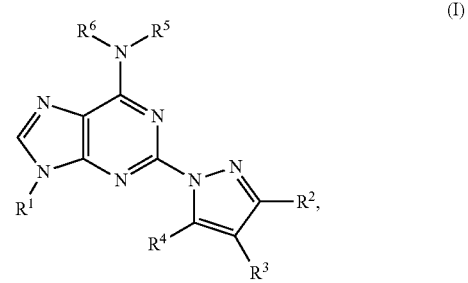

(I)

wherein $R^1$ represents hydrogen or alkyl; one of $R^2$, $R^3$ and $R^4$ represents alkyl, hydroxy-alkyl, alkoxy-alkyl, halo, trifluoromethyl, trifluoromethoxy, hydroxy or alkoxy; and the other two of $R^2$, $R^3$ and $R^4$, independently of each other, represent hydrogen, alkyl, hydroxy-alkyl, alkoxy-alkyl, halo, trifluoromethyl, trifluoromethoxy, hydroxy or alkoxy; $R^5$ represents phenyl optionally substituted with one or more substituents selected from the group consisting of alkyl, halo, trifluoromethyl, trifluoromethoxy, alkoxy and cyano; and $R^6$ represents R'OC(=O)—, wherein R' represents alkyl, alkoxy, alkoxy-alkyl or adamantanyl.

7 Claims, No Drawings

FOREIGN PATENT DOCUMENTS

| | | |
|---|---|---|
| WO | WO 2008/116911 A1 | 10/2008 |
| WO | WO 2008/116912 A2 | 10/2008 |
| WO | WO 2008/116914 A1 | 10/2008 |
| WO | WO 2010/026087 A1 | 3/2010 |
| WO | WO 2010/034706 A1 | 4/2010 |

OTHER PUBLICATIONS

Jacobs et al., "Substituted 2,4-Diaminoquinazolines and 2,4-Diamino-8-Alkylpurines as Antagonists of the Neurokinin-2 (NK2) Receptor", Bioorganic & Medicinal Chemistry Letters, 1995, vol. 5, No. 23, pp. 2879-2884.

* cited by examiner

SUBSTITUTED PURINYL-PYRAZOLE DERIVATIVES AND THEIR USE AS POTASSIUM CHANNEL MODULATORS

CROSS REFERENCE TO RELATED APPLICATIONS

This application is the National Phase of PCT/EP2009/062253 filed on Sep. 22, 2009, which claims priority under 35 U.S.C. 119(e) to U.S. Provisional Application No. 61/100,975 filed on Sep. 29, 2008 and under 35 U.S.C. 119(a) to Patent Application No. PA 2008 01331 filed in Denmark on Sep. 26, 2008, all of which are hereby expressly incorporated by reference into the present application.

TECHNICAL FIELD

This invention relates to novel substituted purinyl-pyrazol derivatives and their use as potassium channel modulating agents. Moreover the invention is directed to pharmaceutical compositions useful for the treatment or alleviation of diseases or disorders associated with the activity of potassium channels.

BACKGROUND ART

Ion channels are transmembrane proteins, which catalyse the transport of inorganic ions across cell membranes. The ion channels participate in processes as diverse as the generation and timing of action potentials, synaptic transmissions, secretion of hormones, contraction of muscles, etc.

All mammalian cells express potassium ($K^+$) channels in their cell membranes, and the channels play a dominant role in the regulation of the membrane potential. In nerve and muscle cells they regulate the frequency and form of the action potential, the release of neurotransmitters, and the degree of broncho- and vasodilation.

From a molecular point of view, the $K^+$ channels represent the largest and most diverse group of ion channels. For an overview they can be divided into five large subfamilies: Voltage-activated $K^+$ channels ($K_v$), long QT related $K^+$ channels (KvLQT), inward rectifiers ($K_{IR}$), two-pore $K^+$ channels ($K_{TP}$), and calcium-activated $K^+$ channels ($K_{ca}$).

The latter group, the $Ca^{2+}$-activated $K^+$ channels, consists of three well-defined subtypes: SK channels, IK channels and BK channels. SK, IK and BK refer to the single-channel conductance (Small, Intermediate and Big conductance K channel). The SK, IK, and BK channels exhibit differences in e.g. voltage- and calcium-sensitivity, pharmacology, distribution and function.

SK channels are present in many central neurons and ganglia, where their primary function is to hyperpolarize nerve cells following one or several action potentials, in order to prevent long trains of epileptogenic activity to occur. The SK channels are also present in several peripheral cells including skeletal muscle, gland cells, liver cells, and T-lymphocytes. The significance of SK channels in normal skeletal muscle is not clear, but their number is significantly increased in denervated muscle, and the large number of SK channels in the muscle of patients with myotonic muscle dystrophia, suggest a role in the pathogenesis of the disease.

Studies indicate that $K^+$ channels may be a therapeutic target in the treatment of a number of diseases including asthma, cystic fibrosis, chronic obstructive pulmonary disease and rhinorrhea, convulsions, vascular spasms, coronary artery spasms, renal disorders, polycystic kidney disease, bladder spasms, overactive bladder, urinary incontinence, bladder outflow obstruction, interstitiel cystitis, irritable bowel syndrome, gastrointestinal dysfunction, secretory diarrhoea, ischaemia, cerebral ischaemia, ischaemic heart disease, angina pectoris, coronary heart disease, traumatic brain injury, Parkinson's disease, dyskinesia, psychosis, anxiety, depression, dementia, memory and attention deficits, Alzheimer's disease, dysmenorrhea, narcolepsy, Reynaud's disease, intermittent claudication, Sjogren's syndrome, migraine, pain, arrhythmia, hypertension, absence seizures, myotonic muscle dystrophia, xerostomi, diabetes type II, hyperinsulinemia, premature labour, hair loss, cancer and immune suppression.

SUMMARY OF THE INVENTION

It is an object of the present invention to provide novel substituted purinyl-pyrazol compounds capable of modulating SK channels, or subtypes of SK channels.

In one aspect, the present invention provides a compound of formula (I)

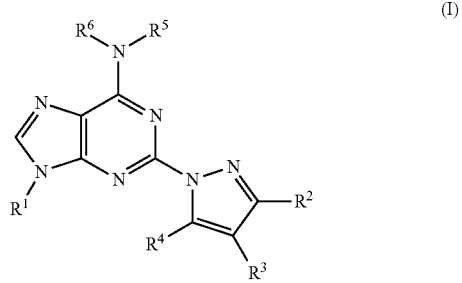

(I)

any of its stereoisomers or any mixture of its stereoisomers, or a pharmaceutically acceptable salt thereof, wherein $R^1$, $R^2$, $R^3$, $R^4$, $R^5$ and $R^6$ are as described below.

In another aspect, the invention provides pharmaceutical compositions comprising an effective amount of a compound of the invention.

In further aspects the invention relates to the use of a derivative of the invention for the manufacture of a medicament for the treatment or alleviation of diseases or disorders associated with the activity of potassium channels, and to method of treatment or alleviation of disorders or conditions responsive to modulation of potassium channels.

DETAILED DISCLOSURE OF THE INVENTION

In one aspect, the present invention provides compounds of formula (I)

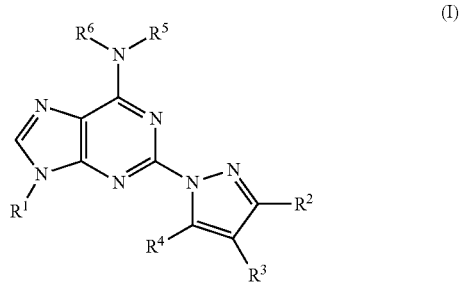

(I)

any of its stereoisomers or any mixture of its stereoisomers, or a pharmaceutically acceptable salt thereof, wherein
$R^1$ represents hydrogen or alkyl;
one of $R^2$, $R^3$ and $R^4$ represents alkyl, hydroxy-alkyl, alkoxy-alkyl, halo, trifluoromethyl, trifluoromethoxy, hydroxy or alkoxy; and the other two of $R^2$, $R^3$ and $R^4$, independently of each other, represent hydrogen, alkyl, hydroxy-alkyl, alkoxy-alkyl, halo, trifluoromethyl, trifluoromethoxy, hydroxy or alkoxy;
$R^5$ represents phenyl optionally substituted with one or more substituents selected from the group consisting of alkyl, halo, trifluoromethyl, trifluoromethoxy, alkoxy and cyano; and
$R^6$ represents R'OC(=O)—, wherein R' represents alkyl, alkoxy, alkoxy-alkyl or adamantanyl.

In one embodiment of the invention, in formula (I), $R^1$ represent hydrogen. In another embodiment, $R^1$ represent alkyl, e.g. methyl.

In another embodiment of the invention, in formula (I), one of $R^2$, $R^3$ and $R^4$ represents alkyl, halo or trifluoromethyl; and the other two of $R^2$, $R^3$ and $R^4$, independently of each other, represent hydrogen, alkyl, halo or trifluoromethyl. In another embodiment one of $R^2$, $R^3$ and $R^4$ represents alkyl or halo; and the other two of $R^2$, $R^3$ and $R^4$, independently of each other, represent hydrogen, alkyl or halo. In another embodiment one of $R^2$, $R^3$ and $R^4$ represents alkyl; and the other two of $R^2$, $R^3$ and $R^4$ independently of each other, represent hydrogen, alkyl or halo. In another embodiment one of $R^2$, $R^3$ and $R^4$ represents alkyl; and the other two of $R^2$, $R^3$ and $R^4$ independently of each other, represent hydrogen or alkyl. In another embodiment one of $R^2$, $R^3$ and $R^4$ represents alkyl; and the other two of $R^2$, $R^3$ and $R^4$ represent hydrogen. In another embodiment all of $R^2$, $R^3$ and $R^4$ represent alkyl.

In another embodiment of the invention, in formula (I), $R^2$ represents alkyl, and $R^3$ and $R^4$ independently of each other, represent hydrogen or alkyl. In another embodiment $R^2$ and $R^4$ represent alkyl, and $R^3$ represents hydrogen.

In another embodiment of the invention, in formula (I), $R^2$ represents alkyl, e.g. methyl.

In another embodiment of the invention, in formula (I), $R^3$ represents hydrogen.

In another embodiment of the invention, in formula (I), $R^4$ represents alkyl, e.g. methyl.

In another embodiment of the invention, in formula (I), $R^5$ represents phenyl optionally substituted with one or more substituents selected from the group consisting of alkyl, halo and trifluoromethyl. In another embodiment $R^5$ represents phenyl. In another embodiment $R^5$ represents phenyl substituted with one or more substituents selected from the group consisting of alkyl, halo and trifluoromethyl. In another embodiment $R^5$ represents phenyl substituted with one substituent selected from the group consisting of alkyl, halo and trifluoromethyl. In another embodiment $R^5$ represents phenyl substituted with one alkyl. In another embodiment $R^5$ represents phenyl substituted with methyl. In another embodiment $R^5$ represents phenyl substituted with one halo. In another embodiment $R^5$ represents phenyl substituted with chlorine. In another embodiment $R^5$ represents phenyl substituted with one trifluoromethyl.

In another embodiment of the invention, in formula (I), $R^6$ represents R'OC(=O)—, wherein R' represents alkyl, e.g. ethyl. In another embodiment R' represents isobutyl. In another embodiment R' represents tert.butyl. In another embodiment R' represents alkoxy. In another embodiment R' represents alkoxy-alkyl, e.g. methoxy-ethyl. In another embodiment $R^6$ represents R'OC(=O)—, wherein R' represents adamantanyl.

In another embodiment of the invention, in formula (I), $R^1$ represents alkyl, one of $R^2$, $R^3$ and $R^4$ represents alkyl; and the other two of $R^2$, $R^3$ and $R^4$ independently of each other, represent hydrogen or alkyl, $R^5$ represents phenyl substituted with one halo and $R^6$ represents R'OC(=O)—, wherein R' represents alkyl. In another embodiment $R^1$ represents alkyl, $R^2$ and $R^4$ represent alkyl; $R^3$ represents hydrogen, $R^5$ represents phenyl substituted with one halo and $R^6$ represents R'OC(=O)—, wherein R' represents alkyl. In another embodiment $R^1$ represents alkyl, $R^2$ and $R^4$ represent alkyl; $R^3$ represents hydrogen, $R^5$ represents phenyl substituted with one halo and $R^6$ represents R'OC(=O)—, wherein R' represents adamantanyl. In another embodiment $R^1$ represents methyl, $R^2$ and $R^4$ represent methyl; $R^3$ represents hydrogen, $R^5$ represents phenyl substituted with one chlorine and $R^6$ represents R'OC(=O)—, wherein R' represents ethyl. In another embodiment $R^1$ represents methyl; $R^2$ and $R^4$ represent methyl; $R^3$ represents hydrogen, $R^5$ represents phenyl substituted with one chlorine and $R^6$ represents R'OC(=O)—, wherein R' represents butyl, e.g. isobutyl or tert.butyl.

In another embodiment of the invention, the compound of the invention is:
(4-Chloro-phenyl)-[2-(3,5-dimethyl-pyrazol-1-yl)-9-methyl-9H-purin-6-yl]-carbamic acid 2-methoxy-ethyl ester;
(4-Chloro-phenyl)-[2-(3,5-dimethyl-pyrazol-1-yl)-9-methyl-9H-purin-6-yl]-carbamic acid adamantan-1-yl ester;
(4-Chloro-phenyl)-[2-(3,5-dimethyl-pyrazol-1-yl)-9-methyl-9H-purin-6-yl]-carbamic acid tert-butyl ester;
(4-Chloro-phenyl)-[2-(3,5-dimethyl-pyrazol-1-yl)-9-methyl-9H-purin-6-yl]-carbamic acid ethyl ester;
(4-Chloro-phenyl)-[2-(3,5-dimethyl-pyrazol-1-yl)-9-methyl-9H-purin-6-yl]-carbamic acid isobutyl ester; or
any of its stereoisomers or any mixture of its stereoisomers, or a pharmaceutically acceptable salt thereof.

Any combination of two or more of the embodiments described herein is considered within the scope of the present invention.

Definition of Substituents

As used throughout the present specification and appended claims, the following terms have the indicated meaning:

The term "halo" or "halogen" shall mean fluorine, chlorine, bromine or iodine.

The term "alkyl" as used herein means a saturated, branched or straight hydrocarbon chain, e.g. from one to six carbon atoms ($C_{1-6}$-alkyl; lower alkyl), including pentyl, isopentyl, neopentyl, tertiary pentyl, hexyl and isohexyl. In another embodiment alkyl represents a $C_{1-4}$-alkyl group, including butyl, isobutyl, secondary butyl, and tertiary butyl. In another embodiment of this invention alkyl represents a $C_{1-3}$-alkyl group, which may in particular be methyl, ethyl, propyl or isopropyl.

The term "hydroxy" shall mean the radical —OH.

The term "carbonyl" shall mean the radical —C(=O)—.

The term "alkoxy" as used herein refers to the radical —O-alkyl. Representative examples are methoxy, ethoxy, propoxy (e.g. 1-propoxy, 2-propoxy), butoxy (e.g. 1-butoxy, 2-butoxy, 2-methyl-2-propoxy), pentoxy (1-pentoxy, 2-pentoxy), hexoxy (1-hexoxy, 3-hexoxy), and the like.

The term "trihalomethyl" shall mean trifluoromethyl, trichloromethyl, and similar trihalo-substituted methyl groups.

The term "trihalomethoxy" shall mean trifluoromethoxyl, trichloromethoxy, and similar trihalo-substituted methoxy groups.

The term "hydroxy-alkyl" as used herein refers to alkyl substituted one or more times at any carbon atom(s) with hydroxyl. Representative examples are hydroxymethyl, hydoxyethyl (e.g. 1-hydroxyethyl, 2-hydroxyethyl), and the like.

The term "alkoxy-alkyl" as used herein refers to alkyl substituted one or more times at any carbon atom(s) with alkoxy. Representative examples are methoxymethyl, ethoxymethyl, 2-methoxyethyl, 2-ethoxyethyl, 3-methoxyprop-1-yl, and the like.

The term "optionally substituted" as used herein means that the groups in question are either unsubstituted or substituted with one or more of the substituents specified. When the group(s) in question are substituted with more than one substituent, the substituents may be the same or different.

Certain of the defined terms may occur more than once in the structural formulae, and upon such occurrence each term shall be defined independently of the other.

The term "treatment" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

The terms "disease", "condition" and "disorder" as used herein are used interchangeably to specify a state of a patient which is not the normal physiological state of man.

The term "medicament" as used herein means a pharmaceutical composition suitable for administration of the pharmaceutically active compound to a patient.

The term "pharmaceutically acceptable" as used herein means suited for normal pharmaceutical applications, i.e. giving rise to no adverse events in patients etc.

The term "effective amount" as used herein means a dosage which is sufficient in order for the treatment of the patient to be effective compared with no treatment.

The term "therapeutically effective amount" of a compound as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

Steric Isomers

It will be appreciated by those skilled in the art that the compounds of the present invention may exist in different stereoisomeric forms—including enantiomers, diastereomers and cis-trans-isomers.

The invention includes all such stereoisomers and any mixtures thereof including racemic mixtures.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Moreover, some of the chemical compounds of the invention being oximes, may thus exist in two forms, syn- and anti-form (Z- and E-form), depending on the arrangement of the substituents around the —C=N— double bond. A chemical compound of the present invention may thus be the syn- or the anti-form (Z- and E-form), or it may be a mixture hereof.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention, including compounds modified at one or more reactive or derivatizable groups of the parent compound. Of particular interest are compounds modified at a carboxyl group, a hydroxyl group, or an amino group. Examples of suitable derivatives are esters or amides.

The compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Methods of Preparation

The compounds of the invention may be prepared by conventional methods of chemical synthesis, e.g. those described in the working examples. The starting materials for the processes described in the present application are known or may readily be prepared by conventional methods from commercially available chemicals.

The end products of the reactions described herein may be isolated by conventional techniques, e.g. by extraction, crystallisation, distillation, chromatography, etc.

Biological Activity

The compounds of the invention may be tested for their usefulness as potassium channel modulating agents e.g. such as described in WO 2006/100212.

The compounds of the invention are capable of selectively modulating SK1, SK2 and/or SK3 channels. Therefore, in another aspect, the invention relates to the use of the compounds of the invention for the manufacture of medicaments, which medicament may be useful for the treatment or alleviation of a disease or a disorder associated with the activity of potassium channels, e.g. SK channels, e.g. SK1, SK2 and/or SK3 channels.

In another embodiment, the disease or a disorder associated with the activity of potassium channels is a respiratory disease, epilepsy, convulsions, seizures, absence seizures, vascular spasms, coronary artery spasms, renal disorders, polycystic kidney disease, bladder spasms, overactive bladder (OAB), urinary incontinence, bladder outflow obstruction, interstitiel cystitis (IC), erectile dysfunction, gastrointestinal dysfunction, secretory diarrhoea, ischaemia, cerebral ischaemia, ischaemic heart disease, angina pectoris, coronary heart disease, autism, ataxia, traumatic brain injury, Parkinson's disease, dyskinesia, bipolar disorder, psychosis, schizophrenia, anxiety, depression, mania, mood disorders, dementia, memory and attention deficits, Alzheimer's disease, amyotrophic lateral sclerosis (ALS), dysmenorrhea, narcolepsy, Reynaud's disease, intermittent claudication, Sjogren's syndrome, arrhythmia, hypertension, myotonic muscle dystrophia, spasticity, xerostomi, diabetes type II, hyperinsulinemia, premature labour, hair loss, cancer, irritable bowel syndrome (IBS), immune suppression, migraine or pain, e.g. pelvic pain or abdominal pain, addiction, e.g. drug addiction, drug abuse, cocaine abuse, nicotine abuse, tobacco abuse, alcohol addiction or alcoholism, or withdrawal symptoms caused by the termination of abuse of chemical substances, in particular opioids, heroin, cocaine and morphine, benzodiazepines and benzodiazepine-like drugs, and alcohol.

In another embodiment the disease or a disorder associated with the activity of potassium channels is a respiratory disease, urinary incontinence, erectile dysfunction, anxiety, epilepsy, psychosis, schizophrenia, amyotrophic lateral sclerosis (ALS) or pain.

In another embodiment the disease or a disorder associated with the activity of potassium channels is a respiratory disease, in particular asthma, cystic fibrosis, chronic obstructive pulmonary disease (COPD) or rhinorrhea.

In another embodiment the disease or a disorder associated with the activity of potassium channels is overactive bladder, e.g. urinary incontinence.

In another embodiment the disease or a disorder associated with the activity of potassium channels is epilepsy, seizures, absence seizures or convulsions.

In another embodiment the disease or a disorder associated with the activity of potassium channels is schizophrenia.

In another embodiment the disease or a disorder associated with the activity of potassium channels is addiction.

In another embodiment the disease or a disorder associated with the activity of potassium channels is Parkinson's disease.

In another embodiment the disease or a disorder associated with the activity of potassium channels is pain.

The compounds tested showed a biological activity determined as described herein in the micromolar and sub-micromolar range, i.e. of from below 1 to above 100 µM e.g. from below 0.1 to about 1 µM.

Pharmaceutical Compositions

In yet another aspect the invention provides novel pharmaceutical compositions comprising a therapeutically effective amount of the compounds of the invention.

While a compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers and/or diluents.

In another embodiment, the invention provides pharmaceutical compositions comprising the compound of the invention, or a pharmaceutically acceptable salt or compound thereof, together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Pharmaceutical compositions of the invention may be those suitable for oral, rectal, bronchial, nasal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The derivates of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

For topical administration to the epidermis the chemical compound according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

In one embodiment, the invention provides tablets or capsules for oral administration In another embodiment, the invention provides and liquids for intravenous administration and continuous infusion.

Further details on techniques for formulation and administration may be found in the latest edition of *Remington's Pharmaceutical Sciences* (Maack Publishing Co., Easton, Pa.).

A therapeutically effective dose refers to that amount of active ingredient which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions which exhibit large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated and the route of administration, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, e.g. from about 1 to about 100 mg, e.g. from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Other ranges are from about 0.1 µg/kg to about 10 mg/kg/day i.v., and from about 1 µg/kg to about 100 mg/kg/day p.o.

Methods of Therapy

In another aspect the invention provides a method for the prevention, treatment or alleviation of a disease or a disorder or a condition of a living animal body, including a human, which disease, disorder or condition is responsive to modulation of potassium channels, in particular SK channels, and which method comprises comprising administering to such a living animal body, including a human, in need thereof a therapeutically-effective amount of a compound of the invention.

The indications contemplated according to the invention are those stated above.

It is at present contemplated that suitable dosage ranges are 0.1 to 1000 milligrams daily, 10-500 milligrams daily, or 30-100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Other ranges are from about 0.001 to about 1 mg/kg i.v. and from about 0.1 to about 10 mg/kg p.o.

EXAMPLES

The following examples refer to intermediate compounds and final products for general formula (I) identified in the specification. The preparation of the compounds of general formula (I) of the present invention is described in detail using the following examples. Occasionally, the reaction may not be applicable as described to each compound included within the disclosed scope of the invention. The compounds for which this occurs will be readily recognized by those skilled in the art. In these cases the reactions can be successfully performed by conventional modifications known to those skilled in the art, which is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials.

Example 1

2,6-Dichloro-9-Methyl-9H-Purine and 2,6-Dichloro-7-Methyl-7H-Purine (Intermediate Compounds)

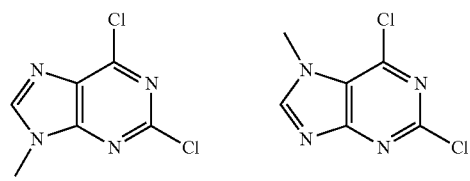

Sodium hydride (60% in mineral oil, 2.53 g, 63.5 mmol) was added to an ice-cooled solution of 2,6-dichloropurine (10.0 g, 52.9 mmol) in tetrahydrofuran (75 mL) and the mixture was stirred for 30 min. Methyl iodide (3.29 mL, 52.9 mmol) was added drop-wise and the reaction mixture was stirred over night. Water was added and the aqueous phase was extracted with ethyl acetate. The combined organic phases were dried over magnesium sulphate, filtered and concentrated in vacuo. Dichloromethane was added and undissolved material was collected by filtration. The crystalline compound turned out to be 2,6-dichloro-7-methyl-7H-purine (1.19 g, 11%) The filtrate was concentrated in vacuo and purified by flash chromatography (ethyl acetate/heptane) to give 2,6-dichloro-9-methyl-9H-purine (3.0 g, 28%).

Example 2

N-(4-Chloro-Phenyl)-Formamide (Intermediate Compound)

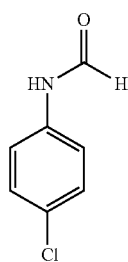

4-Chloroaniline (15 g, 117 mmol) and formic acid (25 mL, 663 mL) were heated to reflux for 2 hours. The mixture was concentrated in vacuo. Saturated aqueous sodium hydrogen carbonate was added and the aqueous phase was extracted twice with ethyl acetate. The combined organic phases were dried over magnesium sulphate, filtered and concentrated in vacuo to give N-(4-chloro-phenyl)-formamide (17.6 g, 97%) as a grey crystalline compound.

Example 3

(2-Chloro-9-Methyl-9H-Purin-6-yl)-(4-Chloro-Phenyl)-Amine (Intermediate Compound)

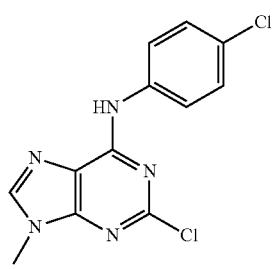

N-(4-Chloro-phenyl)-formamide (766 mg, 4.93 mmol) was dissolved in N,N-dimethylformamide (10 mL). Sodium hydride (60% in mineral oil, 240 mg, 5.91 mmol) was added and the mixture was stirred for 30 min. 2,6-Dichloro-9-methyl-9H-purine (1.0 g, 4.93 mmol) was added and the reaction mixture was heated to 80° C. for 2 hours; cooled to room temperature and poured into water. The resulting precipitate was collected by filtration, washed with water and dried to give (2-chloro-9-methyl-9H-purin-6-yl)-(4-chloro-phenyl)-amine (1.2 g, 4.08 mmol, 83%).

Example 4

(4-Chloro-Phenyl)-(2-Hydrazino-9-Methyl-9H-Purin-6-yl)-Amine (Intermediate Compound)

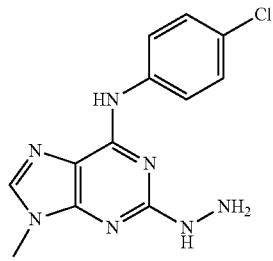

(2-Chloro-9-methyl-9H-purin-6-yl)-(4-chloro-phenyl) amine (3.58 g, 12.1 mmol) was dissolved in tetrahydrofuran (50 mL). Hydrazine monohydrate (26 mL, 536 mmol) was added and the reaction mixture was heated to reflux over night. The next day water was added and the resulting solid was collected by filtration, washed with water and dried to give (4-chloro-phenyl)-(2-hydrazino-9-methyl-9H-purin-6-yl)-amine (3.16 g, 90%) as a white crystalline compound.

Example 5

(4-Chloro-Phenyl)-[2-(3,5-Dimethyl-Pyrazol-1-yl)-9-Methyl-9H-purin-6-yl]-Amine (Intermediate Compound)

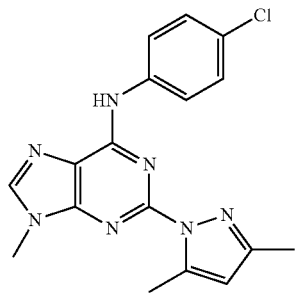

(4-Chloro-phenyl)-(2-hydrazino-9-methyl-9H-purin-6-yl)amine (4.15 g, 14.3 mmol) and 2,4-pentanedione (2.0 mL, 19.1 mmol) in ethanol (100 mL) were heated to reflux for 20 min. Water was added and the white crystalline compound was collected by filtration, washed with water and dried to give (4-chloro-phenyl)-[2-(3,5-dimethyl-pyrazol-1-yl)-9-methyl-9H-purin-6-yl]-amine (4.25 g, 84%).

Example 6

(4-Chloro-Phenyl)-[2-(3,5-Dimethyl-Pyrazol-1-yl)-9-Methyl-9H-Purin-6-yl]-Carbamic Acid 2-Methoxy-Ethyl Ester (Compound 6.1)

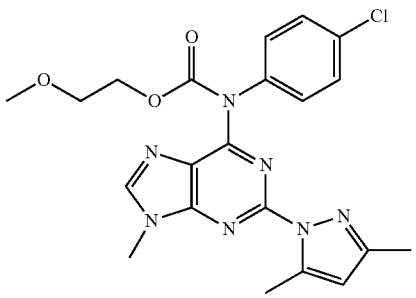

(4-Chloro-phenyl)-[2-(3,5-dimethyl-pyrazol-1-yl)-9-methyl-9H-purin-6-yl]-amine (520 mg, 1.5 mmol) was dissolved in N,N-dimethylformamide (5 mL). Sodium hydride (60% in mineral oil, 90 mg, 2.2 mmol) was added and mixture was stirred at room temperature for 30 minutes. 2-Methoxyethyl chloroformate (0.26 mL, 2.2 mmol) was added and stirring was continued at room temperature over night. Water was added and the aqueous phase was extracted twice with ethyl acetate. The combined organic phases were dried over magnesium sulphate, filtrated and concentrated in vacuo. The crude product was purified by flash chromatography (ethyl acetate/methanol as eluent) to give (4-chloro-phenyl)-[2-(3, 5-dimethyl-pyrazol-1-yl)-9-methyl-9H-purin-6-yl]-carbamic acid 2-methoxy-ethyl ester (280 mg, 42%) as a white solid.

LC-ESI-HRMS of [M+H]+ shows 456.1544 Da. Calc. 456.155091 Da, dev. −1.5 ppm (4-Chloro-Phenyl)-[2-(3,5-Dimethyl-Pyrazol-1-yl)-
9-Methyl-9H-Purin-6-yl]-Carbamic Acid Adaman-
tan-1-yl Ester (Compound 6.2)

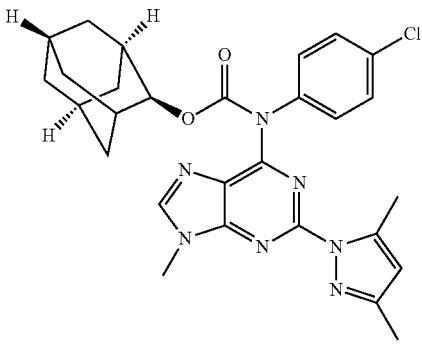

Was prepared according to example 6 from 1-adamanty-
loxycarbonyl fluoride instead of 2-methoxyethyl chlorofor-
mate.

LC-ESI-HRMS of [M+H]+ shows 532.2226 Da. Calc.
532.222776 Da, dev. −0.3 ppm (4-Chloro-Phenyl)-[2-(3,5-Dimethyl-Pyrazol-1-yl)-
9-Methyl-9H-Purin-6-yl]-Carbamic Acid Tert-Butyl
Ester (Compound 6.3)

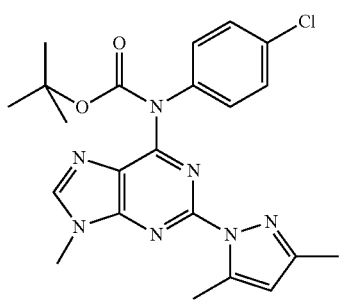

Was prepared according to example 6 from di-tert-butyl-
dicarbonate instead of 2-methoxyethyl chloroformate.

LC-ESI-HRMS of [M−H]− shows 452.1615 Da. Calc.
452.160176 Da, dev. 2.9 ppm (4-Chloro-Phenyl)-[2-(3,5-Dimethyl-Pyrazol-1-yl)-
9-Methyl-9H-Purin-6-yl]-Carbamic Acid Ethyl Ester
(Compound 6.4)

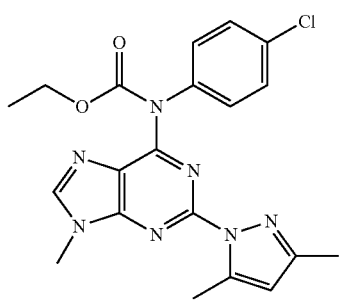

Was prepared according to example 6 from ethylchlorofor-
mate instead of 2-methoxyethyl chloroformate.

LC-ESI-HRMS of [M+H]+ shows 426.1454 Da. Calc.
426.143981 Da, dev. 3.3 ppm (4-Chloro-Phenyl)-[2-(3,5-Dimethyl-Pyrazol-1-yl)-
9-Methyl-9H-Purin-6-yl]-Carbamic Acid Isobutyl
Ester (Compound 6.5)

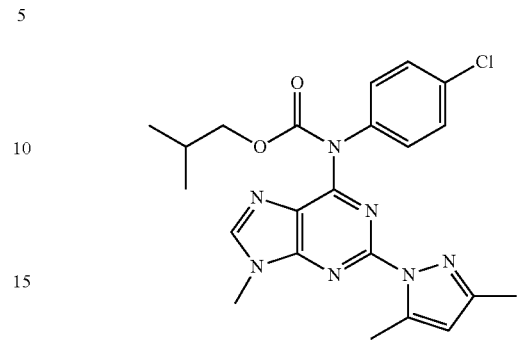

Was prepared according to example 6 from isobutylchlo-
roformate instead of 2-methoxyethyl chloroformate.

LC-ESI-HRMS of [M+H]+ shows 454.1761 Da. Calc.
454.175281 Da, dev. 1.8 ppm

Example 7

Biological Activity

This example demonstrates the biological activity of a
compound representative of the invention (Compound 6.5).
The ionic current through small-conductance $Ca^{2+}$-activated
$K^+$ channels (SK channels, subtype 3) is recorded using the
whole-cell configuration of the patch-clamp technique in a
classic patch-clamp set-up using HEK293 tissue culture cells
expressing hSK3 channels as described in e.g. WO 2006/
100212.

The $SC_{100}$ value determined is defined as the Stimulating
Concentration required for increasing the baseline current by
100%. The $SC_{100}$ value determined for Compound 6.5 of the
invention was 0.3 μM, which is an indication of its SK3
activating properties.

From the foregoing it will be appreciated that, although
specific embodiments of the invention have been described
herein for purposes of illustration, various modifications may
be made without deviating from the spirit and scope of the
invention. Accordingly, the invention is not to be limited as by
the appended claims.

The features disclosed in the foregoing description, in the
claims and/or in the accompanying drawings, may both sepa-
rately and in any combination thereof, be material for realis-
ing the invention in diverse forms thereof.

The invention claimed is:
1. A compound of formula (I)

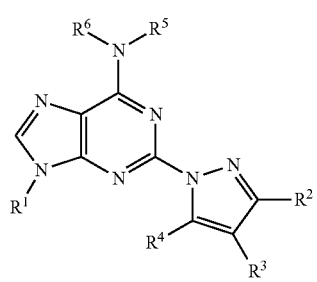

any of its stereoisomers or any mixture of its stereoisomers, or a pharmaceutically acceptable salt thereof, wherein $R^1$ represents hydrogen or alkyl;

one of $R^2$, $R^3$ and $R^4$ represents alkyl, hydroxy-alkyl, alkoxy-alkyl, halo, trifluoromethyl, trifluoromethoxy, hydroxy or alkoxy; and the other two of $R^2$, $R^3$ and $R^4$, independently of each other, represent hydrogen, alkyl, hydroxy-alkyl, alkoxy-alkyl, halo, trifluoromethyl, trifluoromethoxy, hydroxy or alkoxy;

$R^5$ represents phenyl optionally substituted with one or more substituents selected from the group consisting of alkyl, halo, trifluoromethyl, trifluoromethoxy, alkoxy and cyano; and $R^6$ represents R'OC(=O)—, wherein R' represents alkyl, alkoxy, alkoxy-allyl or adamantanyl.

2. The compound according to claim 1, any of its stereoisomers or any mixture of its stereoisomers, or a pharmaceutically acceptable salt thereof, wherein $R^1$ represents alkyl.

3. The compound according to claim 1, any of its stereoisomers or any mixture of its stereoisomers, or a pharmaceutically acceptable salt thereof, wherein $R^2$ and $R^4$ represent alkyl and $R^3$ represents hydrogen.

4. The compound according to claim 1, any of its stereoisomers or any mixture of its stereoisomers, or a pharmaceutically acceptable salt thereof, wherein $R^5$ represents phenyl substituted with halo.

5. The compound according to claim 1, any of its stereoisomers or any mixture of its stereoisomers, or a pharmaceutically acceptable salt thereof, wherein $R^6$ represents R'OC(=O)—, wherein R' represents alkyl.

6. The compound of claim 1, which is:
(4-Chloro-phenyl)-[2-(3,5-dimethyl-pyrazol-1-yl)-9-methyl-9H-purin-6-yl]-carbamic acid 2-methoxy-ethyl ester;
(4-Chloro-phenyl)-[2-(3,5-dimethyl-pyrazol-1-yl)-9-methyl-9H-purin-6-yl]-carbamic acid adamantan-1-yl ester;
(4-Chloro-phenyl)-[2-(3,5-dimethyl-pyrazol-1-yl)-9-methyl-9H-purin-6-yl]-carbamic, acid tert-butyl ester;
(4-Chloro-phenyl)-[2-(3,5-dimethyl-pyrazol-1-yl)-9-methyl-9H-purin-6-yl]-carbamic acid ethyl ester;
(4-Chloro-phenyl)-[2-(3,5-dimethyl-pyrazol-1-yl)-9-methyl-9H-purin-6-yl]-carbamic acid isobutyl ester; or
a pharmaceutically acceptable salt thereof.

7. A pharmaceutical composition comprising a therapeutically-effective amount of a compound according to claim 1, any of its stereoisomers or any mixture of its stereoisomers, or a pharmaceutically acceptable salt thereof, together with at least one pharmaceutically-acceptable carrier or diluent.

* * * * *